US008777884B2

(12) United States Patent
DeHeer et al.

(10) Patent No.: US 8,777,884 B2
(45) Date of Patent: Jul. 15, 2014

(54) HINGED EQUINUS BRACE WITH PEDIATRIC, DIABETIC AND CLUBFOOT VERSIONS

(76) Inventors: Patrick DeHeer, Carmel, IN (US); John H. Moorin, Carmel, IN (US); Ricky Heath, Fishers, IN (US)

(*) Notice: Subject to any disclaimer, the term of this patent is extended or adjusted under 35 U.S.C. 154(b) by 222 days.

(21) Appl. No.: 13/480,430

(22) Filed: May 24, 2012

(65) Prior Publication Data
US 2012/0283613 A1 Nov. 8, 2012

Related U.S. Application Data

(63) Continuation-in-part of application No. 13/439,449, filed on Apr. 4, 2012.

(60) Provisional application No. 61/489,398, filed on May 24, 2011, provisional application No. 61/583,474, filed on Jan. 5, 2012, provisional application No. 61/471,302, filed on Apr. 4, 2011.

(51) Int. Cl.
*A61F 5/00* (2006.01)

(52) U.S. Cl.
USPC .................................. 602/16; 602/23; 602/29

(58) Field of Classification Search
USPC .............................. 602/5, 16, 23–29; 128/882
See application file for complete search history.

(56) References Cited

U.S. PATENT DOCUMENTS

| | | | |
|---|---|---|---|
| 5,393 A | 12/1847 | Chamberlin | |
| 73,768 A | 1/1868 | Allen | |
| 265,942 A | 10/1882 | Burns | |
| 3,958,567 A | 5/1976 | Callender, Jr. | |
| 4,632,096 A | 12/1986 | Harris | |
| 4,981,132 A | 1/1991 | Chong | |
| 5,378,223 A | 1/1995 | Grim et al. | |
| 5,891,071 A * | 4/1999 | Stearns et al. | 602/26 |
| 5,891,077 A * | 4/1999 | Gilman et al. | 602/57 |
| 6,048,326 A * | 4/2000 | Davis et al. | 602/26 |
| 6,096,942 A * | 8/2000 | Hack | 602/41 |
| 6,280,404 B1 | 8/2001 | Morinaka et al. | |
| 7,077,818 B2 | 7/2006 | Ingimundarson et al. | |
| 2004/0002672 A1 | 1/2004 | Carlson | |
| 2009/0069732 A1 | 3/2009 | Jackovitch | |
| 2013/0247421 A1* | 9/2013 | Santos | 36/100 |

FOREIGN PATENT DOCUMENTS

| | | |
|---|---|---|
| DE | 102008052369 | 10/2008 |
| DE | 102008052517 | 7/2010 |

OTHER PUBLICATIONS

J A Radford, et al., "Does stretching increase ankle dorsiflexion range of motion? A systematic review." Br J Sports Med, Aug. 22, 2006, pp. 870-875, 40.

* cited by examiner

*Primary Examiner* — Michael A. Brown
(74) *Attorney, Agent, or Firm* — D'Hue Law LLC; Cedric A. D'Hue

(57) ABSTRACT

Devices and processes used to treat ankle equinus for users with specific conditions such as young age, diabetes, or clubfoot. More specifically, the present disclosure relates to a brace and the corresponding method of use to treat equinus by stretching the Gastrocnemius muscle.

18 Claims, 14 Drawing Sheets

HINGED EQUINUS BRACE WITH PEDIATRIC, DIABETIC AND CLUBFOOT VERSIONS

REFERENCE TO RELATED APPLICATIONS

The present application is a continuation-in-part of application Ser. No. 13/439,449, filed Apr. 4, 2012, which claims priority from U.S. Provisional Patent Application Ser. No. 61/489,398, which was filed May 24, 2011, under the title "Hinged Equinus Brace with Toe Wedge" and U.S. Provisional Patent Application Ser. No. 61/583,474, which was filed Jan. 5, 2012, under the title "Adjustable-Sole, Hinged Equinus Brace with Toe Wedge," and U.S Provisional Patent Application Ser. No. 61/471,302,which was filed Apr. 4, 2011, under the title "Equines Brace," the disclosures of which are expressly incorporated by reference.

FIELD

The present disclosure relates to devices and processes used to treat ankle equinus. More specifically, the present disclosure relates to braces or device and their methods of use to treat equinus by stretching the Gastrocnemius muscle and/or the Soleus muscle.

BACKGROUND

Equinus is typically described as a condition in which the upward bending motion of the ankle is limited. Equinus is defined as the inability or lack of ankle joint dorsiflexion less than a right angle relative to the leg.

Equinus may result in a lack of flexibility past the right angle relative to the leg. Someone suffering with equinus may lack the flexibility to bring the top of foot 18 past a right angle (90°) relative to the leg and toward the front of the leg. A typical maximum ankle range of motion for dorsiflexion is indicated as twenty-five degrees (25°) less than a right angle relative to the leg. Equinus may also be characterized as a limited ankle range of motion for dorsiflexion which is no more than five (5°), ten (10°) or even fifteen degrees (15°) less than a right angle relative to the leg.

There are several possible causes for limited range of ankle motion. Limited range of ankle motion is often due to tightness in the calf muscles (the soleus muscle and/or the gastrocnemius muscle). Shortening of the gastrocnemius muscle (also known as gastroc equinus) is a very common condition which may affect most people because the gastrocnemius muscle crosses two joints. The gastrocnemius muscle originates above knee 12 joint, while the soleus originates below knee 12 joint. Both muscles join to form the Achilles tendon, which attaches to the heel. Therefore, the gastrocnemius muscle crosses two joints: knee 12 and the ankle, while the soleus muscle only crosses the ankle joint.

Regardless of the cause of limited ankle motion, someone suffering with equinus can develop a wide range of foot problems. There are several ways to treat limited ankle range of motion, such as gastroc equinus, including stretching exercises, orthotics with heel lifts, padding, molded shoes, serial casting, as well as night splints and braces.

Many current night splints allow user 22 to sleep with their knees bent. Current night splints and braces do not lock knee 12 into extension as they do not extend above the knee. Failure to lock knee 12 into extension means that a person experiencing gastroc equinus does not stretch gastrocnemius muscle, and therefore is only stretching the soleus muscle.

Many current night splints and braces are awkward and uncomfortable for sleeping. Since night splints and many current braces are supposed to be worn throughout the night, an awkward or cumbersome night splint or brace may cause a user to either not get a good night's sleep or cause a user to remove the device. If user 22 does not get a good night's sleep, user 22 may not choose to use the device in the future. This lack of compliance leads to the current devices not performing their intended function.

Even if a knee is kept completely straight by a user, the night splint or brace is not the reason for a complete stretch of gastrocnemius muscle, because there is no above the knee extension locking the knee joint.

If the night splint or brace does not lock the knee in full extension while dorsiflexing the ankle joint, the device is not providing the preferred method of treatment.

DESCRIPTION

For the purpose of promoting an understanding of the principles of the invention, reference will now be made to certain embodiments illustrated in the disclosure, and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figures 1, 2:
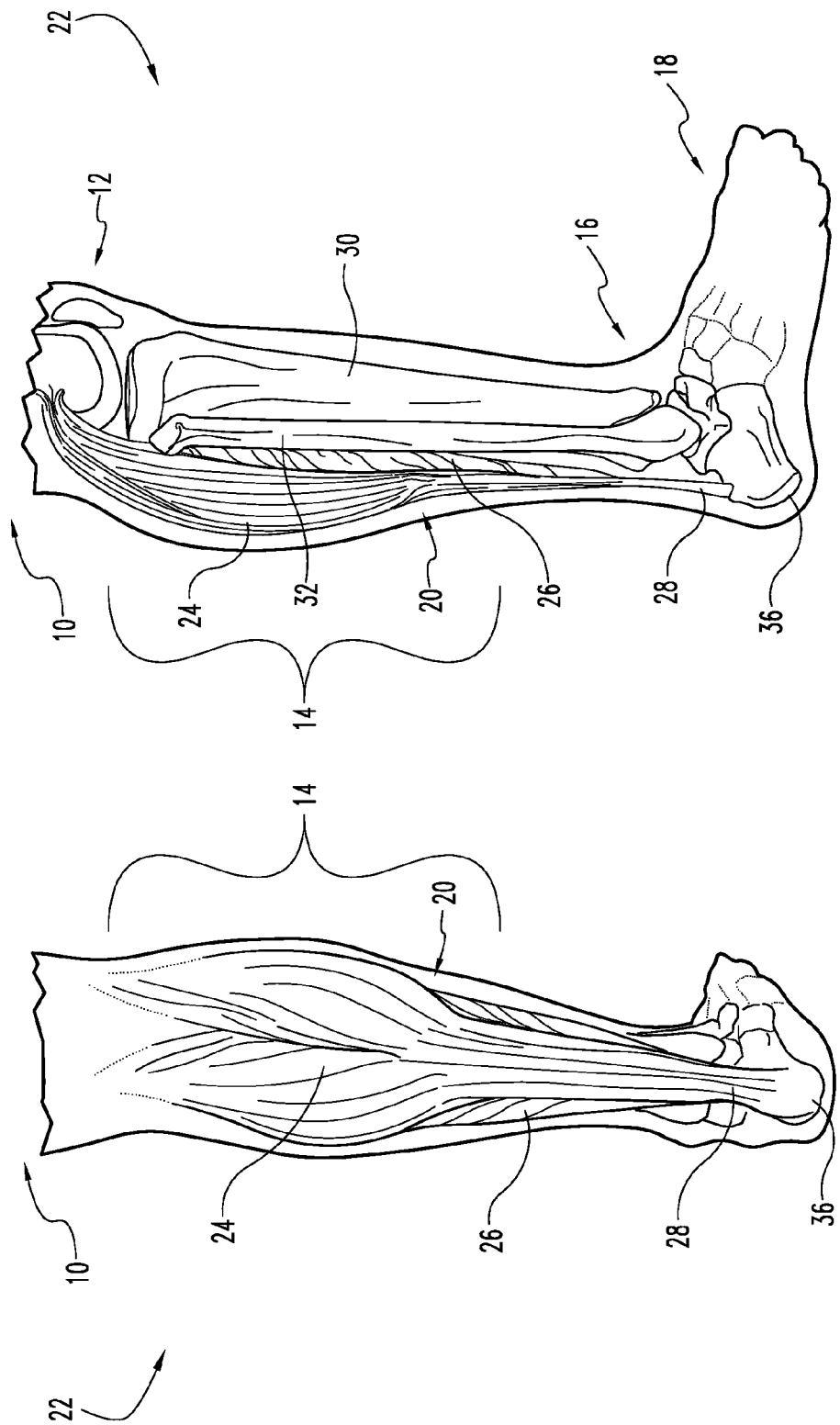
FIG. 1 is a back view of calf muscles with a knee at extension and an ankle at neutral position.
FIG. 2 is a side view of the calf muscles of FIG. 1.

As shown in FIGS. 1 and 2, thigh 10, knee 12, calf 14, ankle 16, foot 18, and calf muscles 20 of user 22 are illustrated. Calf muscles 20 are shown as gastrocnemius muscle 24 and soleus muscle 26. Each of these muscles 24, 26 shares a common insertion (attachment) via Achilles tendon 28 into the posterior calcaneus. Soleus muscle 26 originates at the proximal to medial portions of tibia 30 and fibula 32. Soleus muscle 26 and gastrocnemius muscle 24 unite via their respective apponeurosis to form Achilles tendon 28. Unlike soleus muscle 26, gastrocnemius muscle 24 originates at posterior femur 34 just above knee 12 and also inserts into heel 36. Gastrocnemius muscle 24 crosses two joints: knee 12 and ankle 16.

As illustrated with knee 12 in extension and ankle 16 in normal position, soleus muscle 26 and gastrocnemius muscle 24 are not stretched to capacity in a person with normal ankle range of motion including maximum ankle dorsiflexion of twenty-five degrees (25°). In a person with limited ankle range of motion, such as equinus, soleus muscle 26 or gastrocnemius muscle 24 may be stretched to capacity with knee 12 in extension for gastroc equinus or gastrosoleal equinus and ankle 16 in normal position or in a dorsiflexed position.

Figure 3:
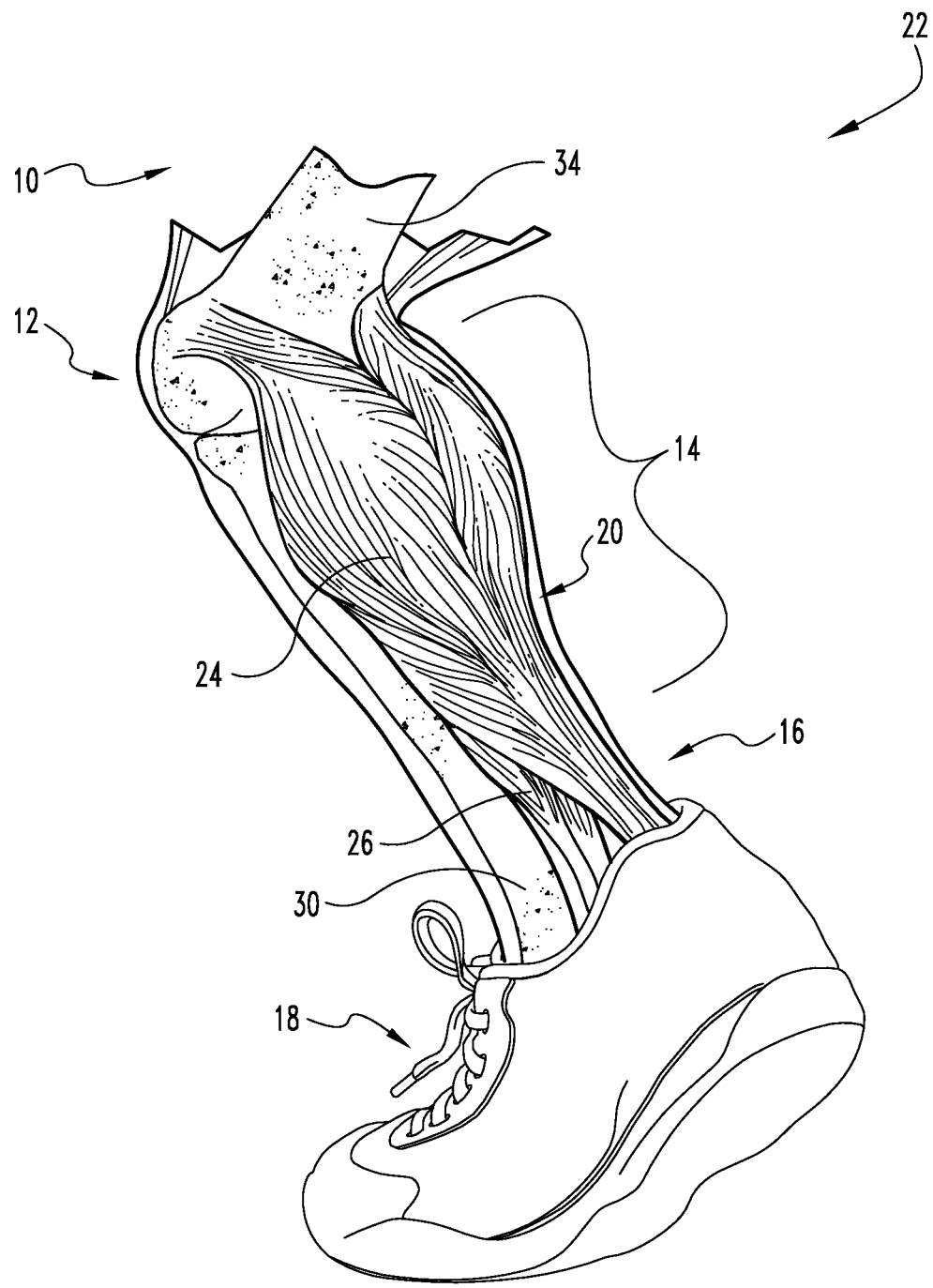
FIG. 3 is a perspective view of calf muscles with a knee in flexion and the ankle in dorsiflexion.

As illustrated in FIG. 3, a person with limited ankle range of motion due to gastroc equinus, moving knee 12 from extension to flexion releases gastrocnemius muscle 24 from full stretch capacity. A person suffering from gastroc equinus may be able to place ankle 16 in dorsiflexion with knee 12 in flexion even though gastrocnemius muscle 24 is shortened.

Figure 4:
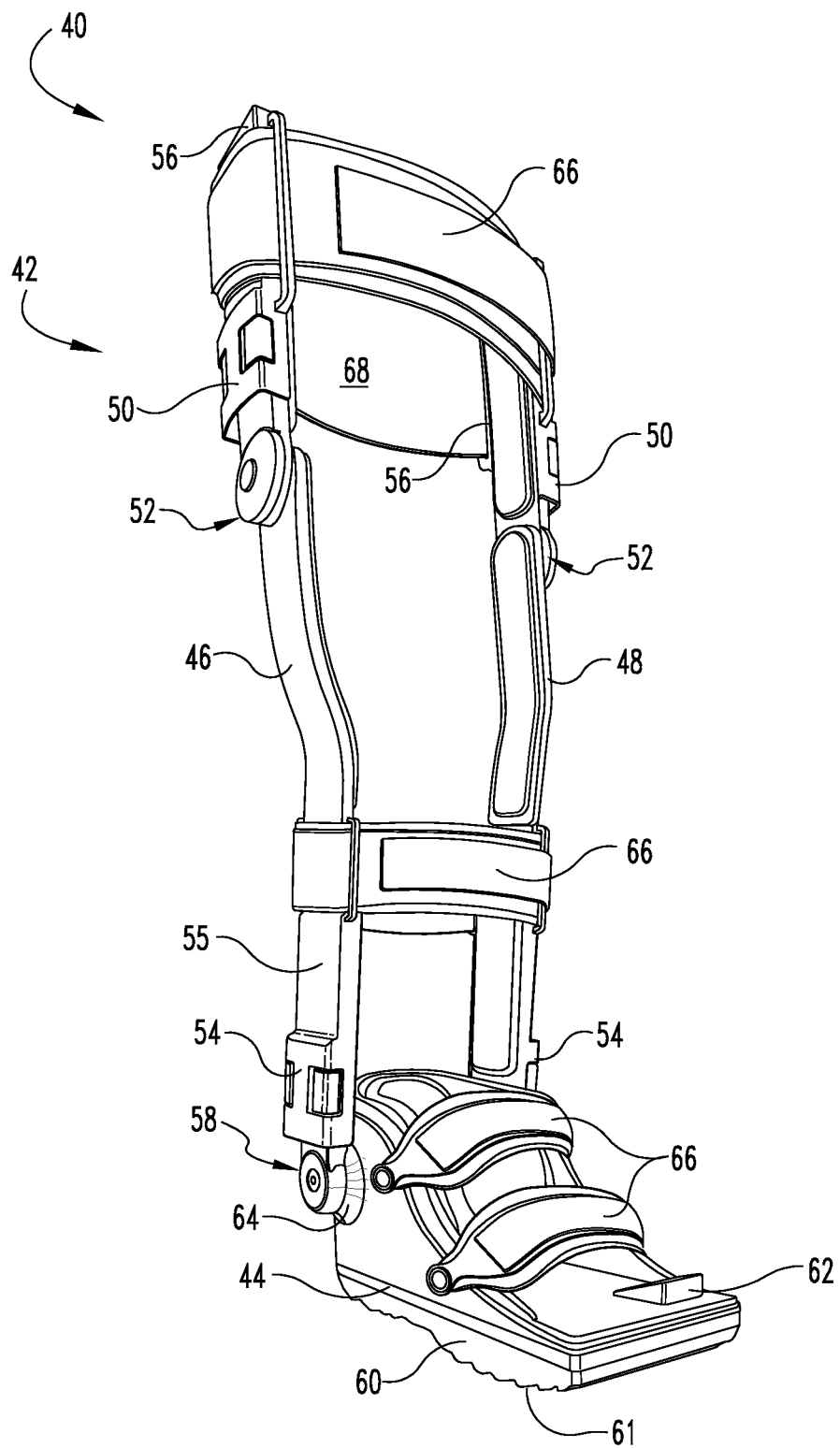
FIG. 4 is a perspective view of a brace/device according to an embodiment of the present disclosure.

Device 40 according to an embodiment of the present disclosure is illustrated in FIG. 4. Device 40 is constructed from plastic molded shell 42 including footplate 44, medial rod 46 and lateral rod 48. Medial rod 46 and lateral rod 48 are each terms used to describe a plurality of elongated rods 46, 48 and additional components. Medial rod 46 and lateral rod 48 each extend from above knee 12 of user 22 to foot 18 of user 22.

Medial rod 46 is described to correspond to the medial side of the leg of user 22. Lateral rod 48 is described to correspond to the lateral side of the leg of user 22. It is understood that in this embodiment each elongated rod can function as either medial rod 46 or lateral rod 48 depending upon the needs of user 22. It is envisioned that device 40 can be used on either leg of user 22. It is also envisioned that by switching device 40 from one leg of user 22 to the other leg of user 22, medial rod 46 becomes lateral rod 48 and vice versa.

Medial rod 46 and lateral rod 48 each include femur adjustment 50, knee hinge 52, and tibia adjustment 54. Femur adjustment 50 includes a slidably attached extension to femur rod 56 of either medial rod 46 or lateral rod 48. Femur adjustment 50 allows for proper sizing and fit of device 40 about the thigh of user 22. In one embodiment, femur adjustment 50 independently extends femur rod 56 to about the middle of thigh 10 of user 22. Femur adjustment 50 also facilitates use of device 40 with users of varying leg length.

Knee hinge 52 connects at least two of the plurality of elongated rods 46, 48. Knee hinge 52 is configured to be located somewhat at, below or above knee 12 of user 22.

Knee hinge 52 allows for anterior or posterior rotation of at least one of the plurality of elongated rods 46, 48. Rotation of femur rod 56 may aid in insertion of user's leg into device 40 or removal of user's leg from device 40. Knee hinge 52 also includes a locking feature which allows knee 12 of user 22 to be locked in extension. As discussed in greater detail below, locking knee in extension aids in stretching the gastrocnemius muscle of user 22. In the alternative, knee hinge 52 also allows for unlocking of knee 12 of user 22 in flexion. Unlocking knee 12 of user 22 in flexion may aid in isolated stretching of the soleus muscle of user 22.

Tibia adjustment 54 provides a slidably attached extension between tibial rod 55 of either medial rod 46 or lateral rod 48 and components of footplate 44. Tibia adjustment 54 allows for proper sizing and fit of device 40 about the lower leg or calf 14 of user 22. Tibia adjustment 54 also facilitates use of device 40 with users of varying leg length.

Furthermore, independent tibia adjustment 54 allows for medial rod 46 and lateral rod 48 to have different heights. As illustrated in FIG. 4, knee hinges 52 for medial rod 46 and lateral rod 48 share the same axis of rotation. However, knee hinges 52 are not required to be coaxial or may be coaxial. Device 40 with non-coaxial knee hinges 52 may be useful for a user having Genu Varum, Genu Valgum, Tibial Varum, or Tibial Valgum deformity. Device 40 with multiaxial ankle hinges 58 may be useful to provide ankle dorsiflexion of user 22 and correction of forefoot varus, forefoot valgus, rearfoot varus, or rearfoot valgus.

Footplate 44 is described as the base of device 40 and support for foot 18 of user 22. Footplate 44 is well padded, including heel 36. It is also envisioned that footplate 44 defines a rear opening to visually confirm seating of heal of user 22. Footplate 44 is also adjustable in width from narrow to wide for wider legs or feet 18 of user 22.

Footplate 44 is also adjustable to allow for shoe size-based adjustment from back to front. This shoe size adjustment ranges in various embodiments from children's size 1 pediatric shoes to adult size 24. Adjustment would vary by device 40 depending on the target user group. For example, one common size range adjusts from size 6 female to size 14 male.

Pediatric versions of device 40 are also envisioned. The size of footplate 44, medial rod 46 and lateral rod 48 are all configured to accommodate children and young adults. These size adjustments range in various embodiments from children's size to young adult size 24.

Multiple sizes of device 40 are envisioned for patients of multiple age groups.

TABLE 1

Summary of pediatric version size descriptions, measurements, and age groups

| Brace Size Description | Brace Sizes (children/adult) | Foot Plate Length | Age Group |
|---|---|---|---|
| Infant brace size | 0.5 to 5 | 3.25" to 4.75" | 0 to 12 months |
| Kid brace size 1 | 55.5 to 9 | 5" to 6.125" | 1 to 5 years |
| Kid brace size 2 | 9.5 to 12 | 6.25" to 7.125" | 1 to 5 years |
| Youth brace size 1 | 12.5 to 3.0 (adult) | 7.25" to 8.5" | 6 to 10 years |
| Youth brace size 2 | 3.5 to 7 (both adult) | 8.625" to 9.75" | 6 to 10 years |

As shown in Table 1, for infants, device 40 may include infant brace sizes from 0.5 to 5. These infant brace size measurements correspond with footplate 44 lengths within the range of approximately 3.25" to approximately 4.75". These infant brace size measurements are configured for patients within the range of approximately 0 months of age to approximately 12 months of age. The ratio of the foot plate 44 length to the lengths of medial rod 46 and lateral rod 48 would be the same based on the foot plate length as stated above.

Footplate 44 includes ankle hinge 58, sole 60, and optional toe wedge 62. Ankle hinge 58 connects medial rod 46 and lateral rod 48 to footplate 44. Ankle hinge 58 is configured to be located adjacent to the ankle of user 22.

Ankle hinge 58 allows for plantarflexion and dorsiflexion of the ankle of user 22. Ankle hinge 58 allows for precise control of ankle position of user 22. Ankle hinge 58 also includes a locking feature which allows user's ankle to be locked in any position, such as normal, plantarflexion or dorsiflexion. In combination with other components of device 40, ankle hinge 58 aids in stretching user's gastrocnemius and soleus muscles, among other things. Specifically, ankle hinge 58 allows for locking user's ankle in dorsiflexion while knee hinge 52 allows for locking user's knee in extension. The combination of knee in extension and ankle in dorsiflexion aids in full stretching of the gastrocnemius and soleus muscles of user 22.

Footplate 44 also includes goniometer 64 located near ankle hinge 58. Goniometer 64 allows for precise measurement of user's ankle position. It is also envisioned that external locking systems, such as a lockout pin (not shown), may be utilized to hold footplate 44 at a prescribed ankle position. This requested ankle position can be precisely measured, monitored, or adjusted with reference to goniometer 64.

Sole 60 is removably coupled to the bottom side of footplate 44 and includes tread pattern 61 to prevent slippage. As shown in FIG. 4, sole 60 is illustrated as a negative heel rocker sole. Negative heel rocker sole 60 is useful for walking or standing with fixed dorsiflexion ankle joint position. Multiple negative heel rocker soles 60 are available at varying angles to match different angles of dorsiflexion. For example, negative heel rocker sole 60 may have five-degree (5°), ten-degree (10°), and fifteen-degree (15°) angles. Additional negative heel rocker sole degree angles are envisioned.

Toe wedge 62 is optionally included with footplate 44. Toe wedge 62 is configured to be located beneath the hallux of user 22. Toe wedge 62 is configured to engage user's Windlass Mechanism, which dorsiflexes the hallux to tighten the plantar fascia thereby supinating the hindfoot and further stretching the Gastrocsoleus complex and additionally the plantar fascia. Multiple toe wedges 62 are available at varying angles. For example, toe wedges 62 may have any degree from thirty degree (30°) to ninety degree (90°) angles. Additional toe wedge angles are envisioned. Alternative mechanisms for engaging the Windlass Mechanism are envisioned. For example, a loop of soft rubber may go over the hallux to dorsiflex the ankle of user 22 in order to engage the Windlass Mechanism with a Velcro strap.

Device 40 may also include adjustable straps 66 with optional padding 68 over the thigh, over the lower leg or calf 14, the dorsal midfoot and at ankle 16. Adjustable straps 66 and padding 68 extend about 4-6 cm anterior and posterior above knee 12 of user 22. Additional adjustable straps 66 with pads 68 anterior and posterior to the tibia and calf extending from the tibial tubercle to the inferior border of the calf of user 22 are also envisioned.

Figure 5:
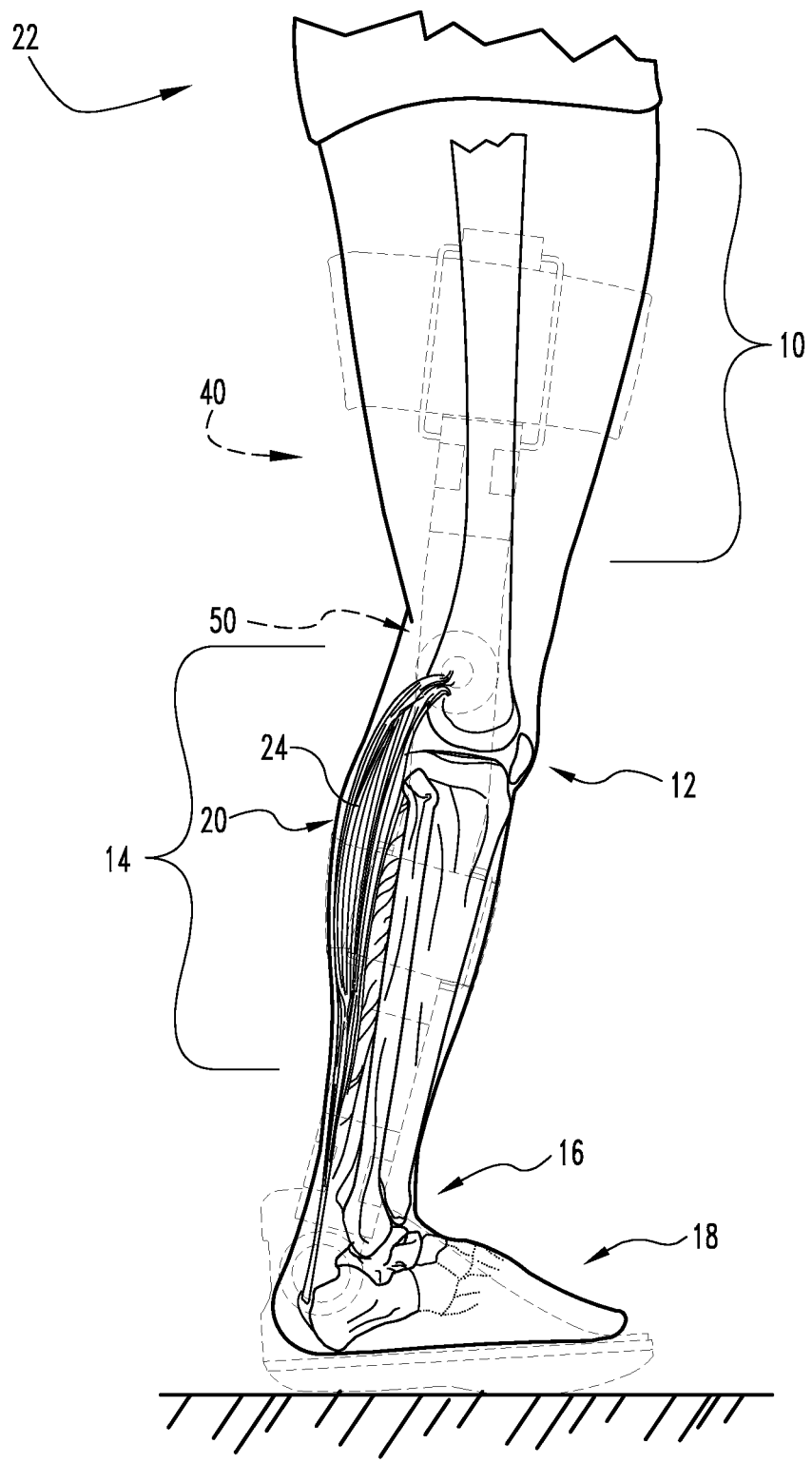
FIG. 5 is a side view of the brace of FIG. 4 and calf muscles with a knee at extension and an ankle in dorsiflexion.

FIG. 5 illustrates device 40 in use by user 22. Device 40 is effective in treating equinus. Device 40 is also effective in treating equinus associated with any of the following other conditions: Heel Spur Syndrome/Plantar fasciitis; neuromuscular disorders such as Cerebral Palsy and Friedreich's Ataxia; congenital disorders such as Congenital Equinus, Clubfoot, Vertical Talus, and, Calcaneal Valgus; Pediatric Flexible Flatfoot deformity; Adult Flexible Flatfoot deformity; Tibialis Posterior Tendon Dysfunction; Achilles tendonitis; Achilles tendon injuries; Haglund's Deformity; Retrocalcaneal heel spurs and tendonosis; Tarsal Coalitions; Bunion deformities; Metatarsalgia; Forefoot pain; Charcot deformity; Diabetic forefoot ulcers and toe ulcers; Equinovarus deformities from post-injury or post-stroke patients; Post Transmetatarsal or Chopart's amputation patients; Midfoot degenerative joint disease at Lis Franc's joint or Chopart's joint; Hypermobile first ray disorders and Cross-over toe deformities.

FIG. 5 is also useful in illustrating methods of treating equinus by stretching user's gastrocnemius muscle. The following illustrated steps of treating equinus using device 40 are: (a) locking knee 12 of user 22 in extension using knee hinge 52 of device 40, (b) locking ankle 16 of user 22 in dorsiflexion using ankle hinge 58 of device 40, thereby stretching user's gastrocnemius muscle 24 and soleus muscle 26. In another embodiment, the additional step of measuring the angle of user's ankle 16 is evident by use of goniometer 64 (FIG. 4) of device 40.

Because device 40 is a targeted stretch of gastrocnemius muscle 24 and soleus muscle 26, device 40 may be used for a shorter period of time than a traditional night splint. Device 40 may yield quicker and more effective results in correction of equinus. Device 40 may provide the same benefit of a traditional night splint without user 22 having to wear device 40 overnight. For example, device 40 worn for two 30 minute sessions per day may provide the same benefit of a traditional night splint worn overnight. This example is based on a meta-analysis by Radford et al. in the British Journal of Sports Medicine 2006. In comparison to a traditional night splint, device 40 may not need to be worn overnight, improving user compliance and providing user with a more comfortable and restful sleep.

Device 40 may be used for a shorter treatment period than other devices. For example, device 40 may be used for one (1) to three (3) months. Some users, especially athletic participants and children, may benefit from a maintenance program after treatment. The maintenance program may involve use of device 40 on a less regular schedule for a period of time to maintain the desired correction.

Device 40 may come with written or digital instructions for users, physicians and therapists. Device 40 may be packaged with Frequently Asked Questions or links to websites for additional information, such as instructions on use.

Figure 6:
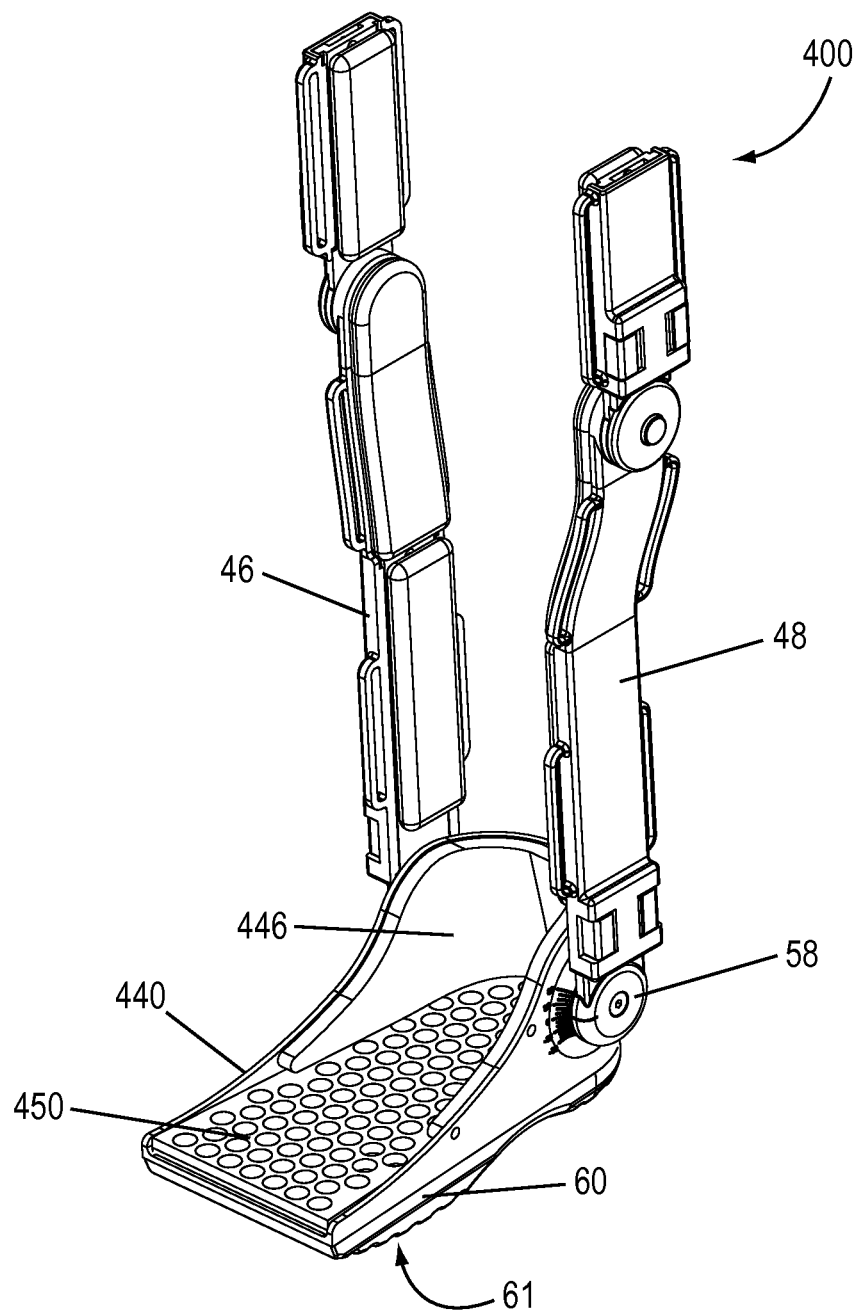
FIG. 6 is a perspective view of a brace/device according to a second embodiment of the present disclosure.
Figure 7:
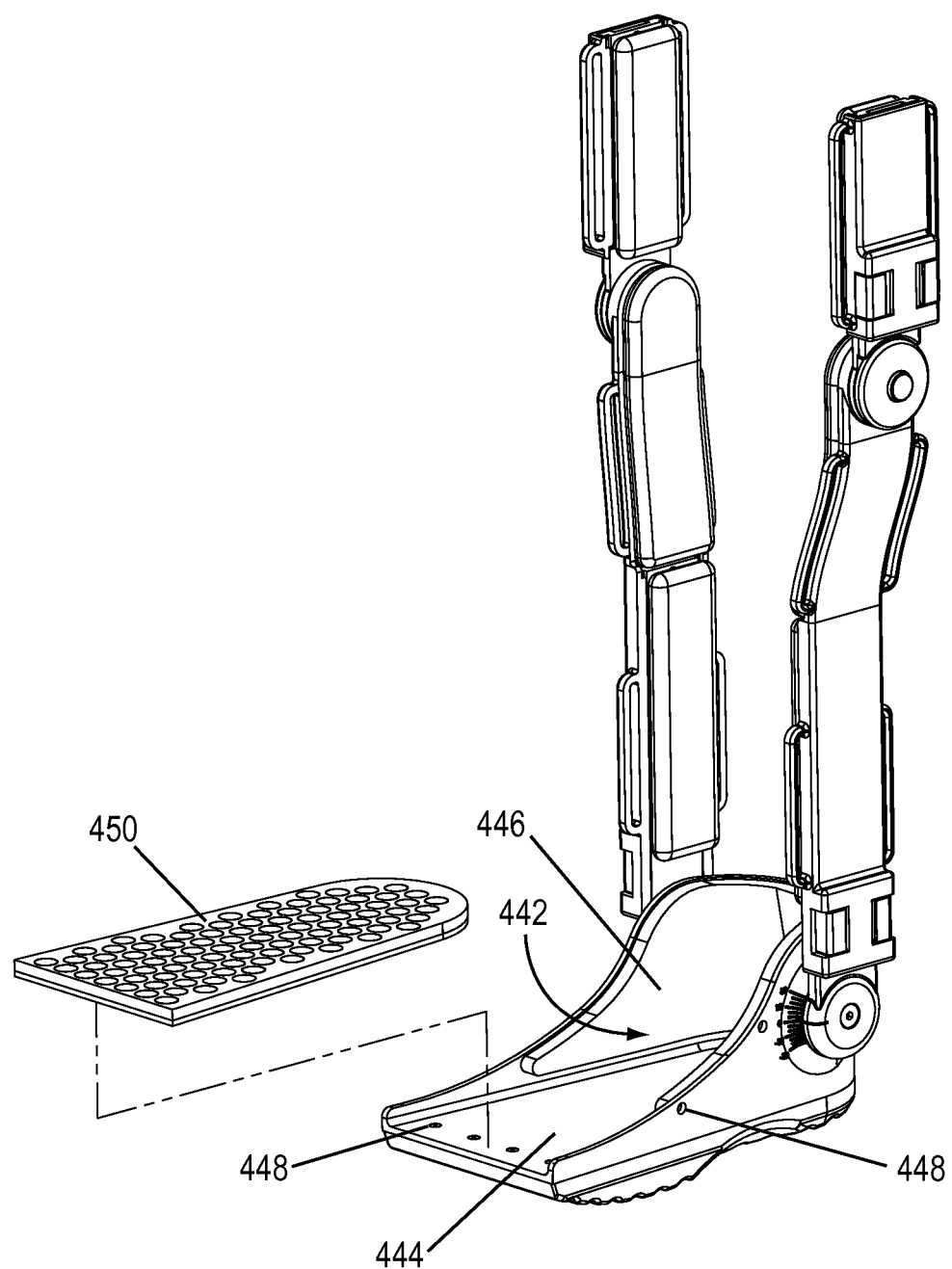
FIG. 7 is an exploded view of the brace/device of FIG. 6.

As illustrated in FIGS. 6 and 7, an alternative embodiment to device 40 is shown as device 400. In this embodiment, similar components and most minor components are not emphasized. Major components such as medial and lateral rods 46 and 48 respectively are shown. The major different components such as footplate 440 and insert 450 are shown and described in detail.

Footplate 440 is similar to footplate 44. Similar components and most minor components are not emphasized. Footplate 440 defines void 442. Void 442 is configured to provide space for insertion of insert 450. Sole 444 of footplate 440 is now configured to attach insert 450 to footplate 440.

Heel support 446 of footplate 440 is also involved in defining void 442. It is also envisioned that heel support 446 may be structured similar to insert 450 to perform functions similar to insert 450. Fasteners 448 may be utilized to attach negative heel rocker sole 60 to footplate 440. Fasteners 448 or other fasteners may also be utilized to attach insert 450 or heel support 446 to footplate 440.

Figure 8:
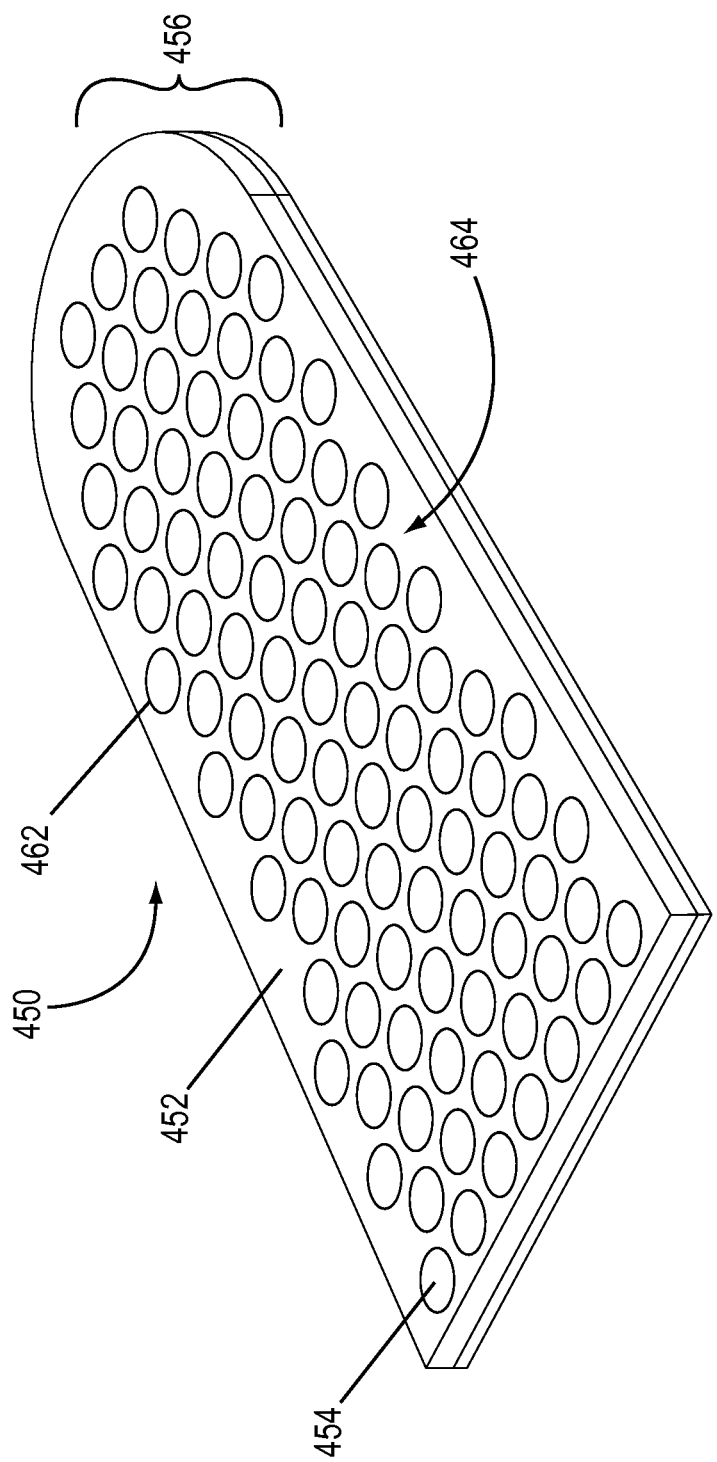
FIG. 8 is a perspective view of an insert according to the second embodiment of the present disclosure.
Figure 9:
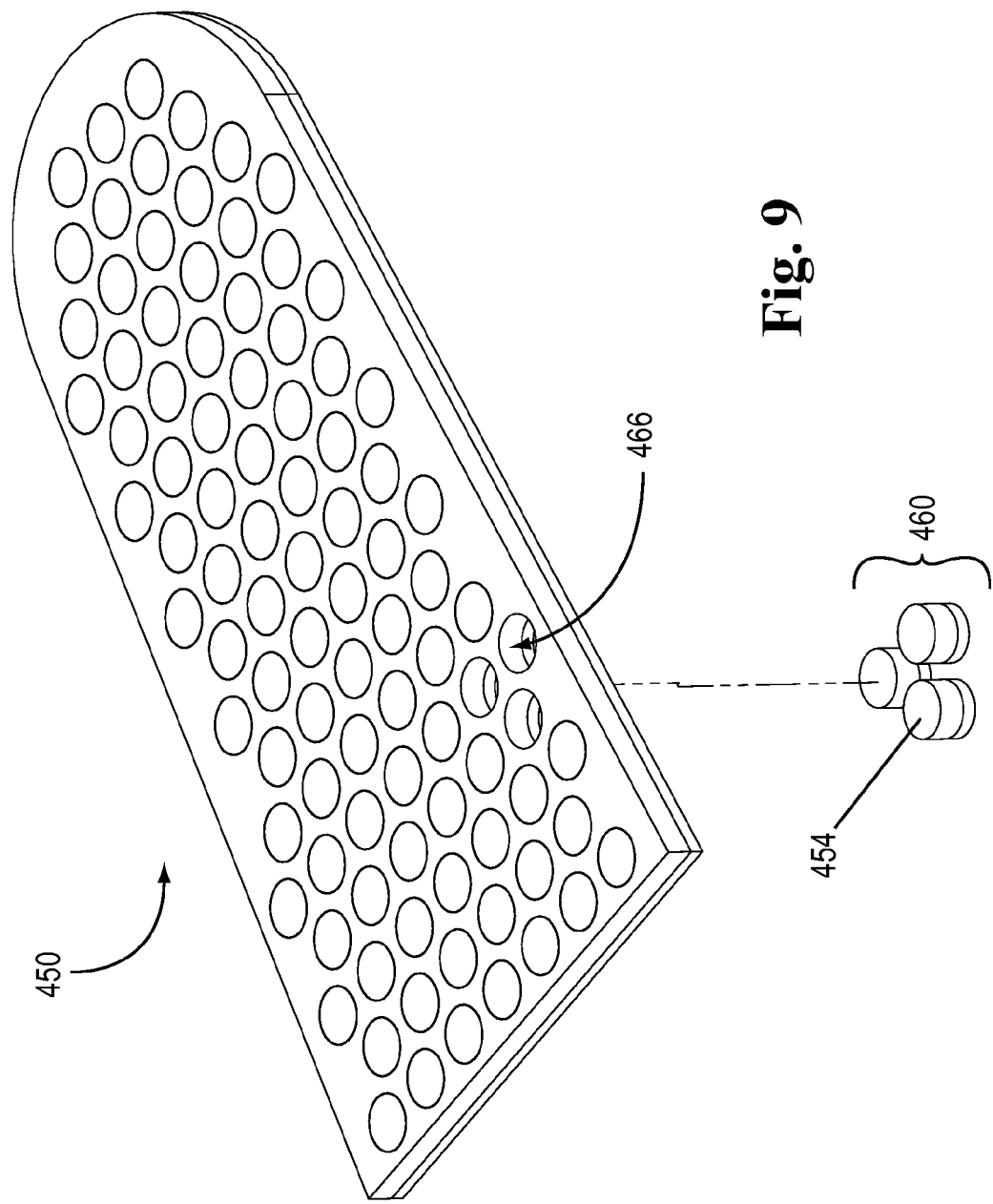
FIG. 9 is an exploded view of the insert of FIG. 8.

As best illustrated in FIGS. 8 and 9, insert 450 is shown as a foot pad. Insert 450 is illustrated to include body 452 and a plurality of removable portions 454. As illustrated, body 452 is comprised of multiple layers 456. Multiple layers 456 may include a layer of laminated material 458 surrounding at least one layer of foam 460. More specifically, the at least one layer of foam 460 may include a plurality of layers of foam such as a base layer (not shown) and a top layer (not shown). In an exemplary embodiment, base layer may be ⅛" thick and include<20 Shore A Closed Cell Foam. In an exemplary embodiment, top layer may be ⅜" thick and include>20 Shore A Closed Cell Foam. The top layer may include additional top layers for several reasons such as the body mass of user 22. The top layer may have removable square plugs that may be configured as initially not separated. The removable square plugs may be removable from the bottom side of insert 450. The top layer may include a thin stretchable top material covering (not shown). The plurality of layers of foam may come in multiple sizes, shapes, and lengths.

Removable portions 454 are shown as either perforated portions 462 of body 452 or are precut portions 462 out of body 452. Perforated or precut portions 462 separate removable portions 454 from body 452 through multiple layers 456.

Perforated or precut portions 462 of one removable portion 454 are not illustrated as touching perforated or precut portions 462 of another removable portion 454. It is also envisioned that perforated or precut portions 462 may touch or intersect other perforated or precut portions 462. Grating 464 of body 452 comprises what would be remaining of body 452 after removal of all removable portions 454.

As evident from FIGS. 8 and 9, substantial portions of body 452 are covered by removable portions 454. As discussed in greater detail below, removable portions 454 are configured for removal to minimize contact between patient's damaged or sensitive tissue and body 452. Stated in another way, removing removable portion 454 allows body 452 to define recess 466. While insert 450 is configured support patient, recess 466 allows patient's damaged or sensitive tissue to not touch insert 450 which may cause additional damage or sensitivity.

As structured, removable portions 454 of insert 450 allow for off-loading of and pre-ulcerative or ulcerative lesion on the plantar aspect of the foot of user 22. Stated another way, insert 450 is helpful in minimizing contact between a patient's diseased tissue and body 452. In operation, a heath care provider may evaluate a patient with diabetes or other similar disease state. A health care provider may also evaluate damaged areas of tissue on the patient. As part of the evaluation and treatment of the patient, the health care provider may chose to remove removable portions 454 which align with damaged areas of tissue. If possible, removal of removable portions 454 may allow insert 450 to support a patient without at least one removable portion 454 touching the patient's damaged areas of tissue.

Figure 10:
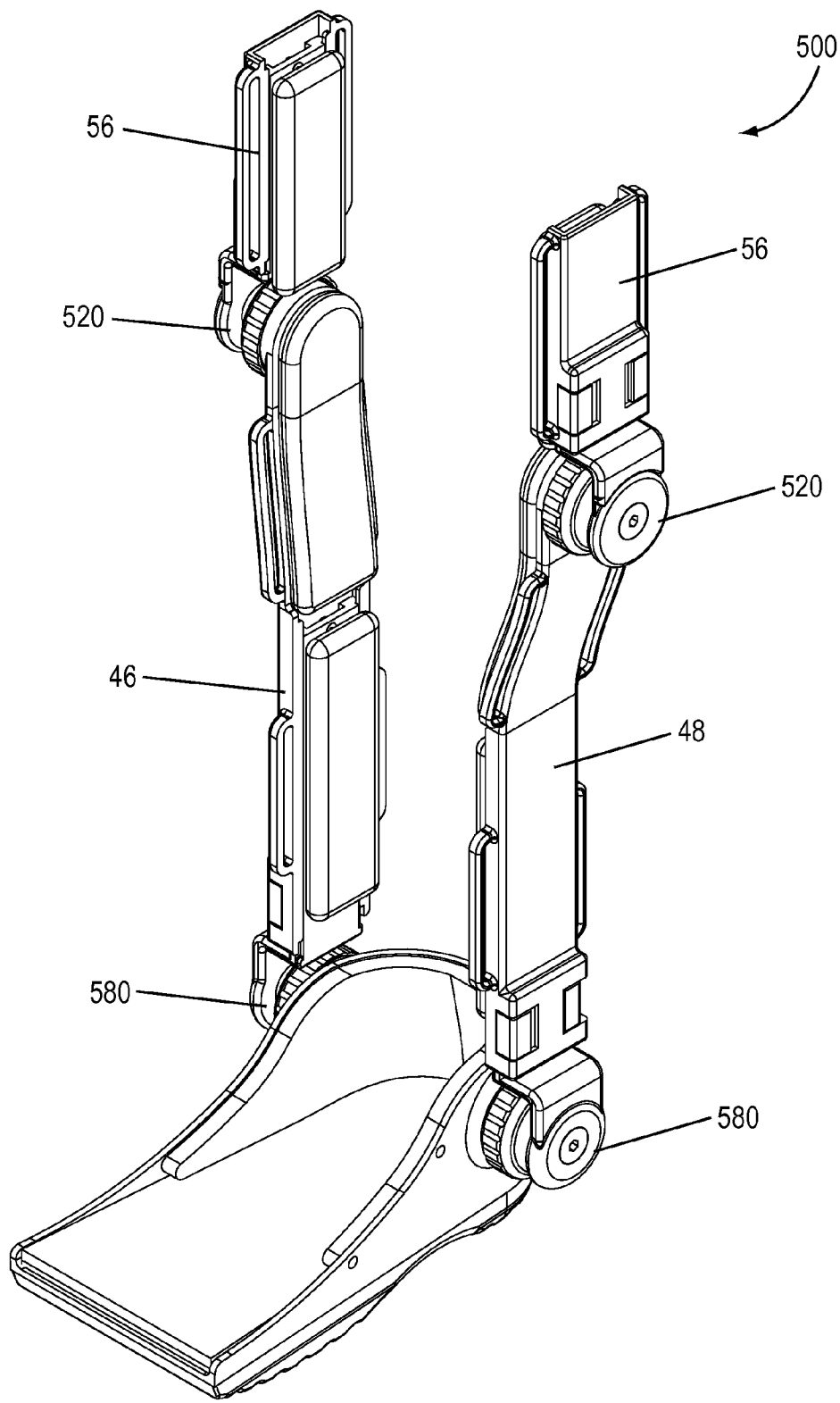
FIG. 10 is a perspective view of a brace/device according to a third embodiment of the present disclosure.
Figure 11:
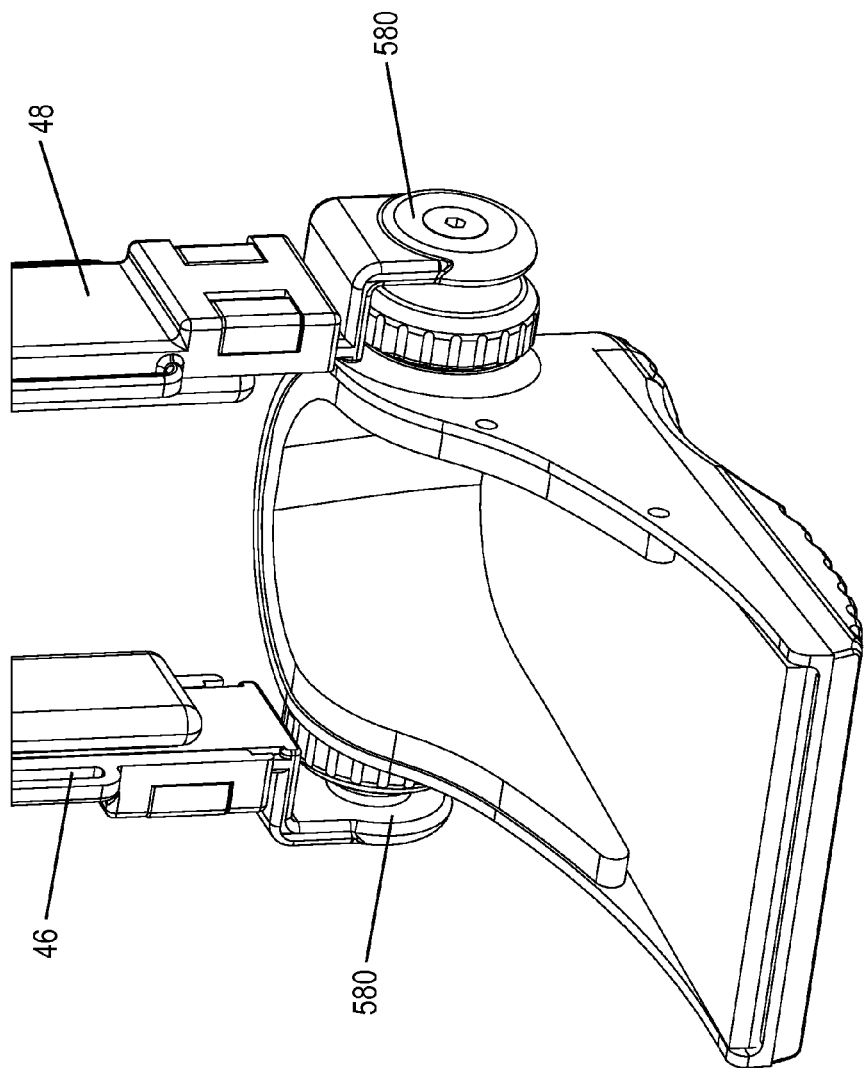
FIG. 11 is another perspective view of the brace/device of FIG. 10.
Figure 12:
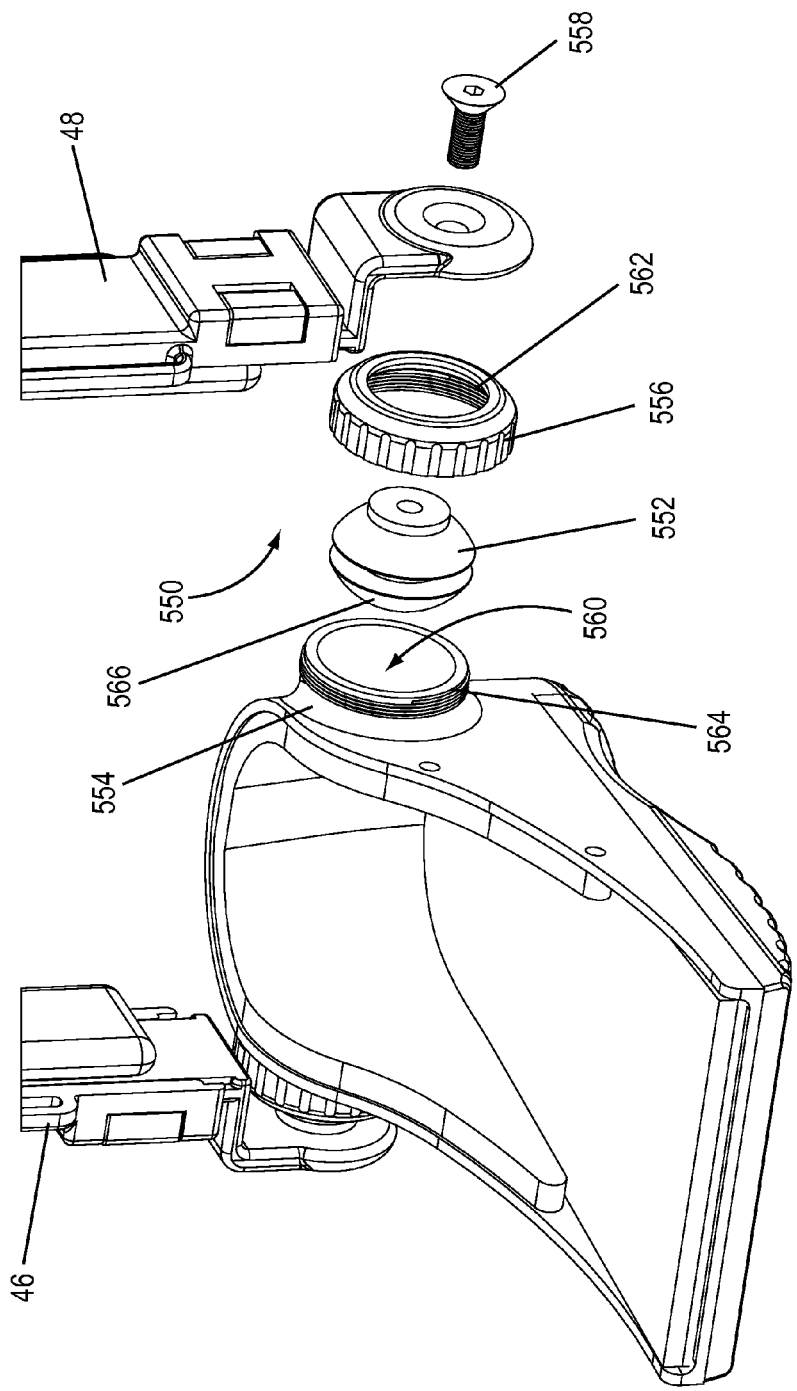
FIG. 12 is an exploded view of the brace/device of FIG. 11.

As illustrated in FIGS. 10, 11, and 12, another alternative embodiment to device 40 is shown as device 500. In this embodiment, similar components and most minor components are not emphasized. Major components such as medial and lateral rods 46 and 48 respectively are shown. The major different components such as knee hinge 520 and ankle hinge 580 are shown and described in detail.

Knee hinge 520 and ankle hinge 580 are different from knee hinge 52 and ankle hinge 58. The major difference is that knee hinge 520 and ankle hinge 580 are multi-axial hinges. As best illustrated in FIG. 12, knee hinge 520 and ankle hinge 580 have a similar configuration including multiaxial hinge configuration 550. Multiaxial hinge configuration 550 is illustrated to include ball 552, socket component 554, cap 556, and fastener 558.

As illustrated a portion of ball 552 fits within void 560 defined by socket component 554. Cap 556 includes threaded members 562 configured to engage with treaded members 564 of socket component 554. As cap 556 tightens on socket component 554, friction band 566 of ball 552 engages socket component 554. Fastener 558 engages ball 552 and a component of either medial or lateral rods 46 and 48, respectively. Multiaxial hinge configuration 550 is locked into a position setting an orientation between footplate 44 and either medial or lateral rods 46 and 48, respectively. When ball 552 is not engaged with socket component 554, ball 552 can rotate changing the orientation between footplate 44 and either medial or lateral rods 46 and 48, respectively. These multiple orientations between footplate 44 and either medial or lateral rods 46 and 48 is an embodiment of a multiaxial hinge.

As illustrated in FIG. 12, multiaxial hinge configuration 550 is a ball and socket configuration. It is also envisioned that a ball & socket configuration is just one method to attain multi-axial movement of medial and lateral rods 46 and 48 with respect to the footplate. Universal joints, stacked-cylinder or piano-hinge joints, and similar structures are all mechanically capable methods of joining two separate bodies and controlling the polar movement with respect to one another. The joints illustrated are an example of one embodiment, but other multi-axial hinge joint combinations are possible.

While knee hinge 520 allows for anterior or posterior rotation of at least one of the plurality of elongated rods 46 and 48, knee hinge 520 also allows for multi-axial rotation of elongated rods 46 and 48. Multiaxial rotation of femur rod 56 may aid in insertion of user's leg into device 500 or removal of user's leg from device 500. Knee hinge 520 also includes a locking feature (not shown) which allows knee 12 of user 22 to be locked in extension. The locking feature of knee hinge 520 also allows components of device 500 to conform to user's leg because knee hinge 520 is also a multiaxial hinge. As discussed in greater detail below, locking knee in extension aids in stretching the gastrocnemius muscle of user 22. In the alternative, knee hinge 520 also allows for unlocking of knee 12 of user 22 in flexion. Unlocking knee 12 of user 22 in flexion may aid in isolated stretching of the soleus muscle of user 22.

Ankle hinge 580 allows for plantarflexion and dorsiflexion of the ankle of user 22 in addition to multiaxial rotation of ankle of user 22. Ankle hinge 580 allows for precise control of ankle position of user 22. Ankle hinge 58 also includes a locking feature which allows user's ankle to be locked in any position, such as normal, plantarflexion or dorsiflexion. In combination with other components of device 40, ankle hinge 58 aids in stretching user's gastrocnemius and soleus muscles, among other things. Specifically, ankle hinge 58 allows for locking user's ankle in dorsiflexion while knee hinge 52 allows for locking user's knee in extension. The combination of knee in extension and ankle in dorsiflexion aids in full stretching of the gastrocnemius and soleus muscles of user 22.

Figure 13:
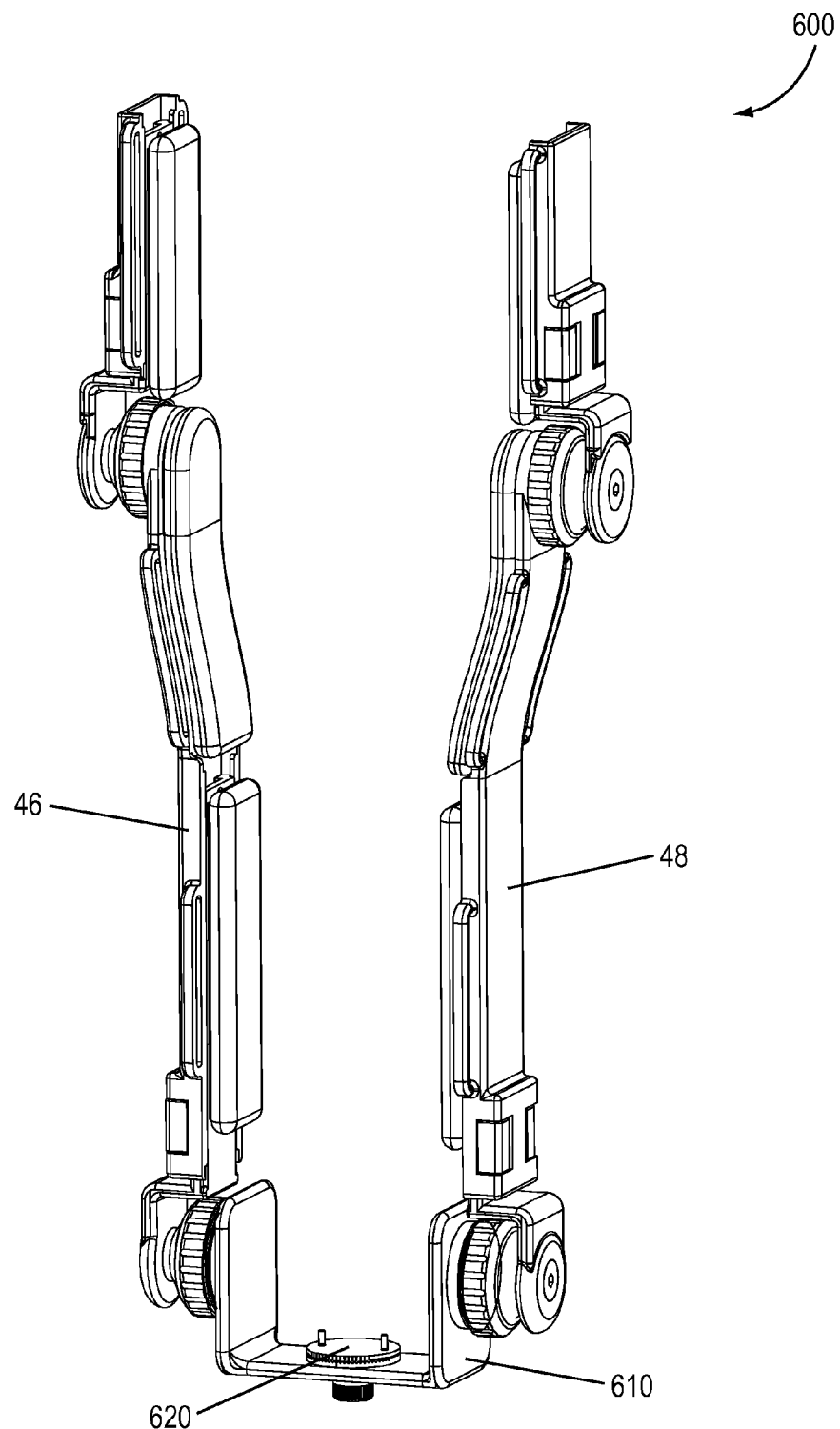
FIG. 13 is a perspective view of a brace/device according to a fourth embodiment of the present disclosure.
Figure 14:
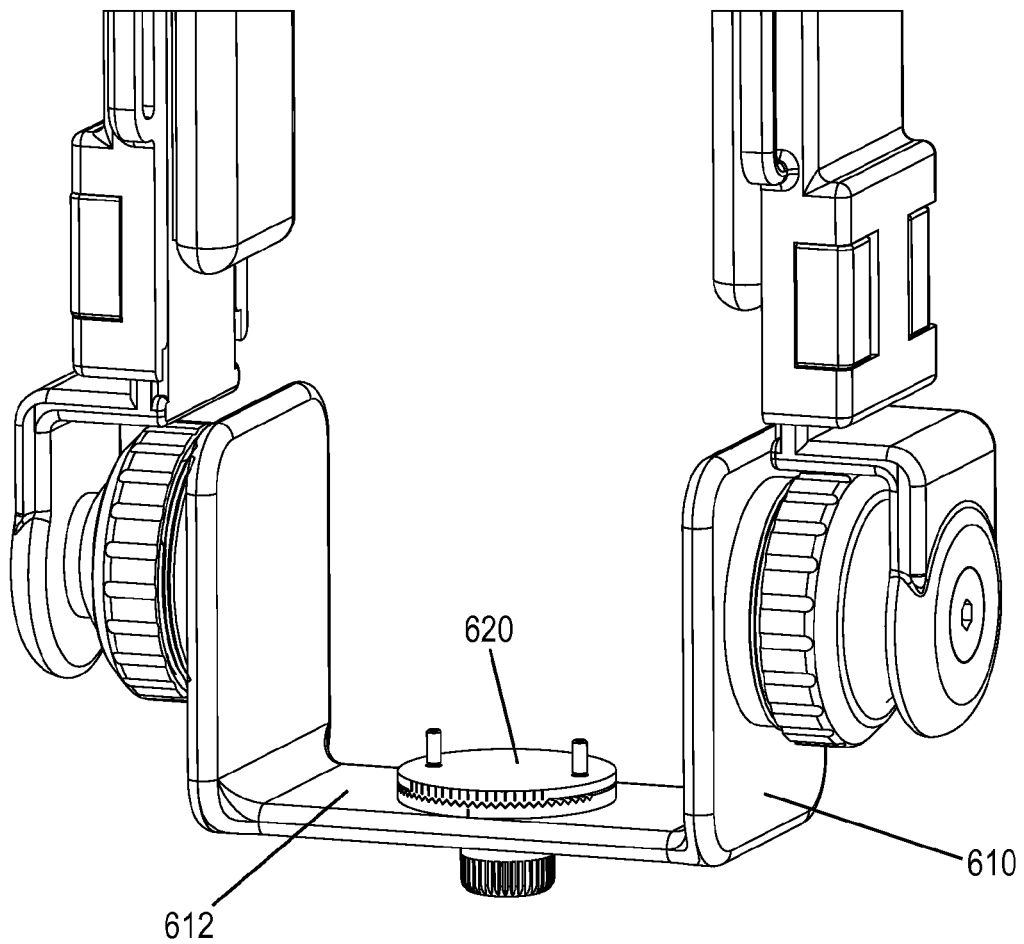
FIG. 14 is another perspective view of the brace/device of FIG. 13.
Figure 15:
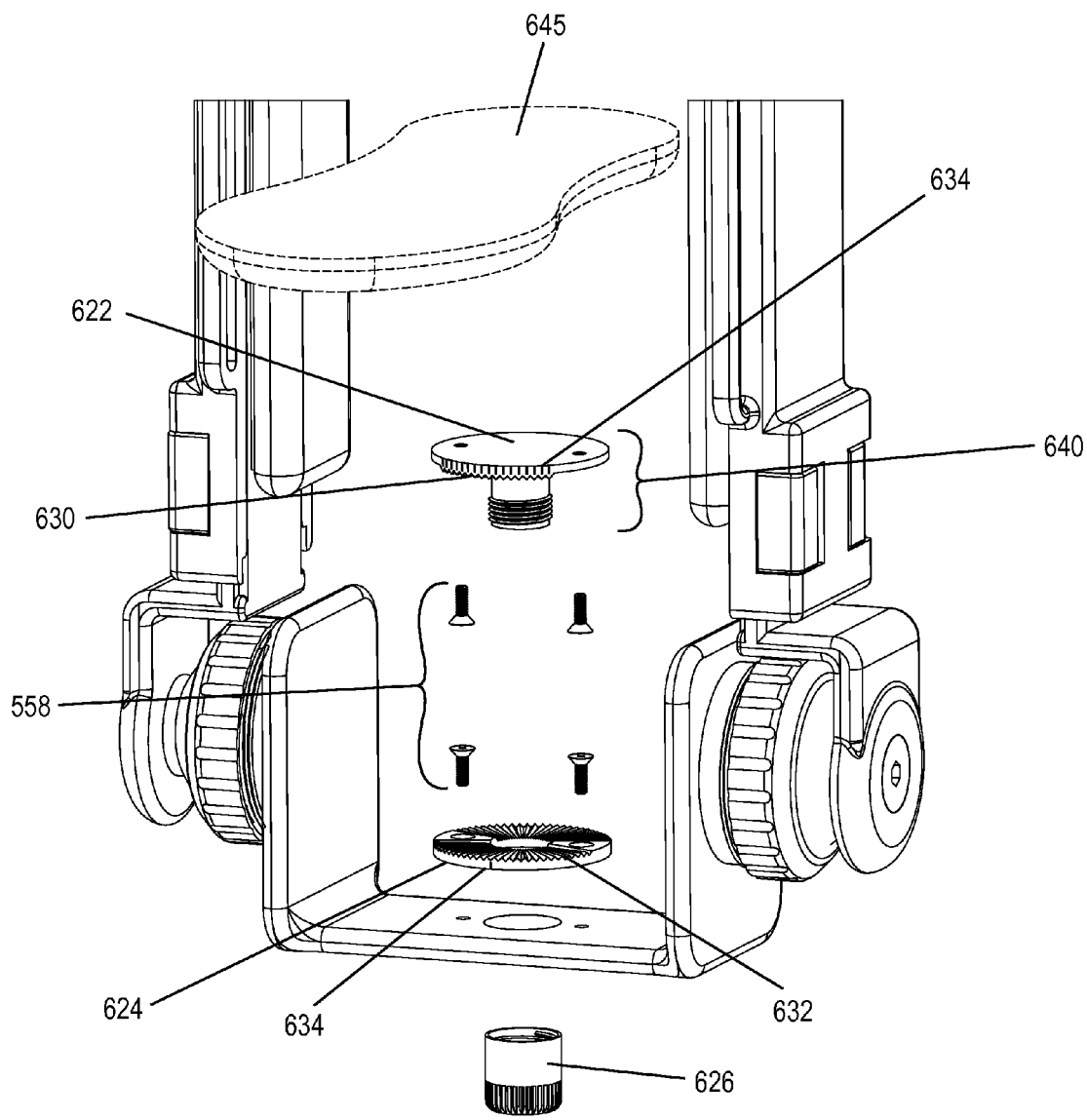
FIG. 15 is an exploded view of the brace/device of FIG. 14.

As illustrated in FIGS. 13, 14, and 15, yet another alternative embodiment to device 40 is shown as device 600. In this embodiment, similar components and most minor components are not emphasized. Major components such as medial and lateral rods 46 and 48 respectively are shown. The major different components such as clubfoot attachment frame 610 and clubfoot attachment system 620 are discussed in greater detail below.

As best illustrated in FIGS. 14 and 15, cross-frame 612 portion of clubfoot attachment frame 610 attaches medial rod 46 to lateral rod 48. In this exemplary embodiment, clubfoot attachment frame 610 replaces a similar function provided by footplate 44. Cross frame 612 portion of clubfoot attachment frame 610 provides direct coupling to clubfoot attachment system 620.

Clubfoot attachment system 620 couples brace 600 to sole 645 of a shoe or other similar device used in a Ponsetti brace for correcting clubfoot. The foot of user 22 is then able to be abducted accordingly and dorsiflexed with multiaxial ankle hinge 580 at the ankle joint, typically abduction is approximately 70 degrees and dorsiflexion is to approximately 5 degrees above 90 degrees. The adjustability of the multiaxial ankle hinge 560 provides the ability for the physician to adjust brace 600 according to the specific needs of the patient.

As best illustrated in FIG. 15, clubfoot attachment system 620 includes boot or brace attachment 622, ring 624, and retention nut 626. Brace attachment 622 includes teeth 630. Teeth 630 are illustrated as located on two sides of brace attachment 622.

Slots 632 are defined by plate 624 and are configured to match teeth 630 creating a locking mechanism about a substantially horizontal plane. Edges 634 of brace attachment 622 and plate 624 illustrate markings corresponding to goniometer 640. Goniometer 640 allows for precise measurement of abduction and dorsiflexion of the treated clubfoot of user 22. The desired foot position can be precisely measured, monitored, or adjusted with reference to goniometer 640.

Brace attachment 622 and plate 624 each utilize fasteners 558. Brace attachment 622 utilizes fasteners 558 to attach to sole 645 of a shoe or other similar device used in a Ponsetti brace. Plate 624 utilizes fasteners 558 to attach to cross-frame 612. Brace attachment 622 utilizes retention nut 626 to create a locking mechanism about a substantially horizontal plane.

In operation, user 22 experiencing clubfoot may apply sole 645 of a shoe or other similar device to the user's foot. The user's shoe is then attached to brace attachment system 620 by use of brace attachment 622. In addition to the previously mentioned functions of device 40, brace 600 assists in treating clubfoot by keeping the user's foot in place.

It is also envisioned that brace 600 acts to correct clubfoot in user 22. Brace 600 may couple to another leg of user 22 or another brace 600 through use of a bar or other device similar to a Dobbs Bar or Dennis-Brown Bar. Brace 600 may also act to correct clubfoot in user 22 only though use of brace 600.

While the inventions have been illustrated and described in detail in the drawings and foregoing description, the same is to be considered as illustrative and not restrictive in character, it being understood that the preferred embodiment has been shown and described and that changes and modifications that come within the spirit of the invention are desired to be protected.

What is claimed is:

1. An insert to a device for treating ankle equinus by stretching the Gastrocnemius muscle and soleus muscle, the insert comprising:
a body comprising multiple layers, wherein multiple layers include a layer of foam and a layer of laminate, and
a plurality of removable portions of the body, wherein the plurality of removable portions are perforated or precut to aid in removal from the body, wherein the plurality of removable portions cover a substantial amount of the body, wherein each of the plurality of removable portions are individually removable from the body, wherein each of the plurality of removable portions are configured to be removed in order to minimize contact between the body and a user's damaged tissue.

2. The insert of claim 1, wherein the removable portions are perforated or precut to a cylindrical shape.

3. The insert of claim 2, wherein the cylindrical shape defines circles on a surface of the body.

4. The insert of claim 2, wherein the perforations of one removable portion do not touch or overlap with the perforations of a second removable portion.

5. The insert of claim 1, wherein the insert is part of a device for treating ankle equinus by stretching the Gastrocnemius muscle and soleus muscle.

6. The insert of claim 5, wherein the device includes:
elongated rods which extend from above the knee of the user to the foot of the user, the rods including a medial elongated rod along a medial side of the leg of the user, the rods including a lateral elongated rod along a lateral side of the leg of the user,
each rod including a locking knee hinge, the locking knee hinge located somewhat at, below or above the knee, the locking knee hinge locking the knee in an extended position at times, the locking knee hinge releasing the knee to a bent position at other times,
each rod including adjustable bars to extend proximally toward the user, the adjustable bars being adjustable to change the overall length of the device to accommodate different leg lengths of different users, and
locking ankle hinges coupling the elongated rods to a footplate, each ankle hinge locking the ankle in a dorsiflexion position at times, each ankle hinge locking the ankle in a normal position or a plantarflexion position at other times.

7. The insert of claim 6, wherein the footplate includes a negative heel rocker sole.

8. The insert of claim 7, wherein the negative heel rocker sole has a degree angle to match an angle of dorsiflexion of the ankle when the ankle hinge locks the ankle in a dorsiflexion position.

9. The insert of claim 6, wherein the ankle hinges each include a goniometer which measures the angle between each elongated rod and the footplate.

10. A method of treating ankle equinus by stretching the Gastrocnemius muscle and soleus muscle of a patient with diabetes, the method comprising the steps of:
providing an insert with removable portions, wherein each of the plurality of removable portions are configured to be removed in order to minimize contact between the body and a patient's damaged tissue,
removing removable portions of the insert in alignment with portions of damaged tissue, and
placing the insert lacking at least one removable portion into a brace for treating ankle equinus by stretching the Gastrocnemius muscle and soleus muscle.

11. The method of claim 10, wherein the step of removing removable portions of the insert in alignment with portions of damaged tissue further comprises the steps of:
removing removable portions such that damaged tissue does not touch the insert.

12. The method of claim 10, wherein the step of removing removable portions of the insert in alignment with portions of damaged tissue further comprises the steps of:
removing removable portions such that damaged tissue does not touch any removable portions of the insert.

13. The method of claim 10, wherein the brace includes:
elongated rods which extend from above the knee of the user to the foot of the user, the rods including a medial elongated rod along a medial side of the leg of the user, the rods including a lateral elongated rod along a lateral side of the leg of the user,
each rod including a locking knee hinge, the locking knee hinge located somewhat at, below or above the knee, the locking knee hinge locking the knee in an extended position at times, the locking knee hinge releasing the knee to a bent position at other times, and
locking ankle hinges coupling the elongated rods to a footplate, each ankle hinge locking the ankle in a dorsiflexion position at times, each ankle hinge locking the ankle in a normal position or a plantarflexion position at other times.

14. The method of claim 13, wherein the locking knee hinge rotates the upper portion of the elongated rod ventral along a sagittal plane of the user to provide easier insertion of the foot and leg of the user.

15. A brace for use by a patient experiencing clubfoot and being treated for ankle equinus by stretching the Gastrocnemius muscle and soleus muscle, the brace comprising:
elongated rods which extend from above the knee of the user to the foot of the user, the rods including a medial elongated rod along a medial side of the leg of the user, the rods including a lateral elongated rod along a lateral side of the leg of the user, each rod including a knee hinge, the knee hinge located somewhat below the knee, the knee hinge locking the knee in an extended position at times, the knee hinge releasing the knee to a bent position at other times, an elongated rod along each side of the leg of the user, the knee hinges positioned coaxial or non-coaxial relative to each other, each of the hinges near the knee of the user, the hinges locking the knee of the user in an extended position at times, the hinges releasing the knee to a bent position at other times, each rod including adjustable bars to extend each rod proximally toward the user, the adjustable bars being adjustable to change the overall length of the device to accommodate different leg lengths of different users, and ankle hinges coupling the elongated rods to an attachment frame including a clubfoot attachment system, each ankle hinge locking the ankle in a dorsiflexion position at some times, each ankle hinge locking the ankle in a normal position or a plantarflexion position at other times, wherein at least one of the knee hinges and the ankle hinges is a multi-axial hinge.

16. The device of claim 15, wherein the multi-axial hinge is a ball and socket configuration.

17. The device of claim 15, wherein the clubfoot attachment system includes brace attachment, ring, and retention nut.

18. The device of claim 15, wherein the equinus is associated with any condition selected from the group consisting of:
 a. Clubfoot
 b. Talipes Equinovarus
 c. Vertical Talus
 d. Talipes Valgus
 e. Talipes Equinovalgus
 f. Talipes Cavus
 g. Talipes Calcaneovalgus and
 h. Talipes Calcaneovarus.

* * * * *